(12) United States Patent
Oguri

(10) Patent No.: US 6,838,482 B2
(45) Date of Patent: Jan. 4, 2005

(54) FUNGICIDAL COMPOSITION

(75) Inventor: Yukio Oguri, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 356 days.

(21) Appl. No.: 10/214,731

(22) Filed: Aug. 9, 2002

(65) Prior Publication Data

US 2003/0055096 A1 Mar. 20, 2003

Related U.S. Application Data

(62) Division of application No. 08/652,576, filed as application No. PCT/JP94/02023 on Dec. 1, 1994, now Pat. No. 6,518,304.

(30) Foreign Application Priority Data

| Dec. 2, 1993 | (JP) | 5-303143 |
| Dec. 27, 1993 | (JP) | 5-333787 |
| Apr. 19, 1994 | (JP) | 6-80219 |
| Apr. 21, 1994 | (JP) | 6-83005 |
| May 13, 1994 | (JP) | 6-99785 |
| May 16, 1994 | (JP) | 6-100833 |
| May 25, 1994 | (JP) | 6-111298 |
| May 30, 1994 | (JP) | 6-116321 |
| Jul. 15, 1994 | (JP) | 6-164180 |
| Jul. 15, 1994 | (JP) | 6-164183 |

(51) Int. Cl.$^7$ .................. A01N 37/12; A01N 47/14
(52) U.S. Cl. ...................... 514/539; 514/483
(58) Field of Search ................ 514/483, 539

(56) References Cited

U.S. PATENT DOCUMENTS

| 5,484,779 A | 1/1996 | Sauter et al. ......... 514/63 |
| 5,500,446 A | 3/1996 | Wingert et al. ....... 514/483 |
| 5,668,163 A | 9/1997 | Dehne et al. ......... 514/376 |

FOREIGN PATENT DOCUMENTS

| EP | 0254426 | 1/1988 |
| EP | 0531837 | 3/1993 |
| EP | 0630570 A2 | 6/1994 |
| EP | 0630570 A3 | 6/1994 |
| EP | 0645084 | 3/1995 |
| EP | 0645087 | 3/1995 |
| EP | 0645088 | 3/1995 |
| EP | 0645089 | 3/1995 |
| EP | 0645091 | 3/1995 |
| GB | 2267644 | 12/1993 |
| JP | 59204165 | 11/1984 |
| JP | 62106084 | 5/1987 |
| JP | 6323852 | 2/1988 |
| JP | 6330463 | 2/1988 |
| JP | 3246268 | 11/1991 |
| JP | 49307 | 1/1992 |
| JP | 4182461 | 6/1992 |
| JP | 4266805 | 9/1992 |
| JP | 4288045 | 10/1992 |
| JP | 5194111 | 8/1993 |

*Primary Examiner*—S. Mark Clardy
(74) *Attorney, Agent, or Firm*—Stevens, Davis, Miller & Mosher, L.L.P.

(57) ABSTRACT

The present invention provides a fungicidal composition characterized by containing as active ingredients (a) a compound represented by the formula I:

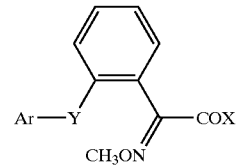

(wherein Ar is a substituted or unsubstituted phenyl group, Y is an oxygen atom, an oxymethylene group or a methyleneoxy group, X is $NR_1R_2$ or $OR_3$, and $R_1$, $R_2$ and $R_3$, which may be the same or different, are hydrogen atoms or alkyl groups having 1 to 4 carbon atoms), and (b) at least one compound selected from the group consisting of ethylenebis(dithiocarbamate) type fungicidal compounds, N-(3,5-dichlorophenyl)imide type fungicidal compounds, Chlorothalonil, phthalimide type fungicidal compounds, anilide type fungicidal compounds, Cymoxanil, Fosetyl, cyanopyrrole type fungicidal compounds, anilino type heterocyclic fungicidal compounds, benzimidazole type fungicidal compounds and their precursors, sulfur, copper compounds, and carbamate type fungicidal compounds for controlling fungi tolerant to benzimidazole type fungicides.

5 Claims, No Drawings

FUNGICIDAL COMPOSITION

CROSS-REFERENCE TO RELATED APPLICATIONS

This application is a divisional application of U.S. patent application Ser. No. 08/652,576, filed Jul. 22, 1996, now U.S. Pat. No. 6,518,304, which, in turn, is a §371 application of international application PCT/JP94/02023, filed Dec. 1, 1994, the entire disclosures of which are herein incorporated by reference, in their entirety.

TECHNICAL FIELD

The present invention relates to a fungicidal composition mainly for agricultural and horticultural use.

BACKGROUND ART

Various agricultural and horticultural fungicides have been known, but there are a great variety of diseases to be controlled and it is difficult to specify the kind of the disease in practice and control the disease by choosing a fungicide suitable for the disease. In addition, it is necessary to cope with the appearance of fungi which have acquired tolerance to specific agents and the occurrence of novel diseases due to the change of the mode of agriculture. For these reasons and the like, there is desired a fungicidal composition having a high activity and a wide anti-microbial spectrum.

The present invention provides a fungicidal composition which has a high activity and a wide antimicrobial spectrum and is markedly effective also against diseases caused by plant pathogenic fungi which have acquired tolerance to certain fungicides.

DISCLOSURE OF THE INVENTION

In detail, the present invention provides a fungicidal composition characterized by containing as active ingredients (a) a compound represented by the formula I:

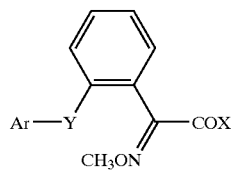

(wherein Ar is a substituted or unsubstituted phenyl group, Y is an oxygen atom, an oxymethylene group or a methyleneoxy group, X is $NR_1R_2$ or $OR_3$, and $R_1$, $R_2$ and $R_3$, which may be the same or different, are hydrogen atoms or alkyl groups having 1 to 4 carbon atoms), and (b) at least one compound selected from the group consisting of ethylenebis(dithiocarbamate) type fungicidal compounds, N-(3,5-dichlorophenyl)imide type fungicidal compounds, Chlorothalonil, phthalimide type fungicidal compounds, anilide type fungicidal compounds, Cymoxanil, Fosetyl, cyanopyrrole type fungicidal compounds, anilino heterocyclic fungicidal compounds, benzimidazole type fungicidal compounds and their precursors, sulfur, copper compounds, and carbamate type fungicidal compounds for controlling fungi tolerant to benzimidazole type fungicides.

The compound of the formula I used in the present invention includes the compounds disclosed in Japanese Patent Unexamined Publication Nos. 63-23852, 3-246268 and 4-288045, etc.

In the formula I, the substituted or unsubstituted phenyl group represented by Ar refers to a phenyl group which may be substituted by one or more substituents selected from alkyl groups having 1 to 4 carbon atoms (e.g. methyl group and ethyl group), halogen atoms (e.g. chlorine atom and bromine atom), haloalkyl groups having 1 to 4 carbon atoms (e.g. trifluoromethyl group), alkoxy groups having 1 to 4 carbon atoms (e.g. methoxy group), haloalkoxy groups (e.g. trifluoromethoxy group), cyano group, etc.

Y is an oxygen atom, an oxymethylene group or a methyleneoxy group, X is $NR_1R_2$ or $OR_3$, and $R_1$, $R_2$ and $R_3$, which may be the same or different, are hydrogen atoms or alkyl groups having 1 to 4 carbon atoms, such as methyl groups.

Some preferable specific examples of the compound of the formula I are given below:

(Ia) methyl α-methoxyimino-2-[(2-methylphenoxy)methyl]phenylacetate

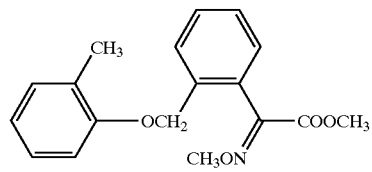

(Ib) N-methyl-α-methoxyimino-2-[(4-chloro-2-methylphenoxy)methyl]phenylacetamide

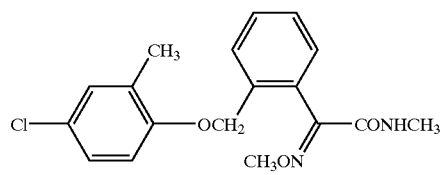

(Ic) N-methyl-α-methoxyimino-2-[(3-chlorophenoxy)methyl]phenylacetamide

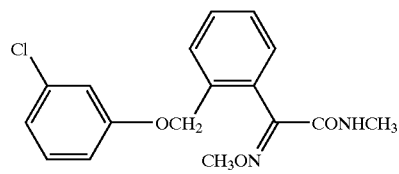

(Id) N-methyl-α-methoxyimino-2-[(2,4-dichlorophenoxy)methyl]phenylacetamide

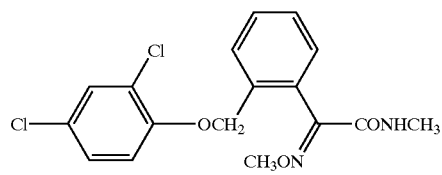

(Ie) N-methyl-α-methoxyimino-2-[(2,5-dimethylphenoxy)methyl]phenylacetamide

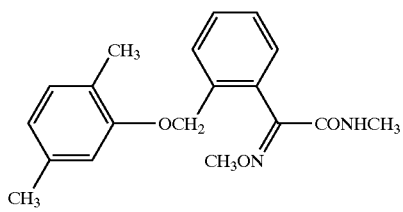

(If) N-methyl-α-methoxyimino-2-[(3-trifluoromethylphenoxy)methyl]phenylacetamide

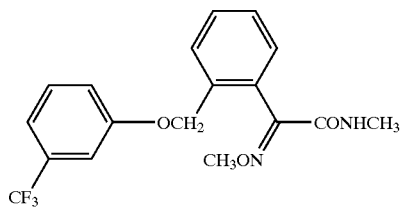

(Ig) N-methyl-α-methoxyimino-2-phenoxyphenylacetamide

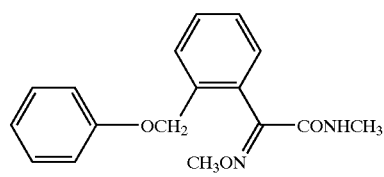

The fungicidal compound(s) used in admixture with the above-mentioned compound is (b) at least one compound selected from the group consisting of ethylene-bis(dithiocarbamate) type fungicidal compounds, N-(3,5-dichlorophenyl)imide type fungicidal compounds, Chlorothalonil (tetrachloroisophthalonitrile), phthalimide type fungicidal compounds, anilide type fungicidal compounds, Cymoxanil, Fosetyl, cyanopyrrole type fungicidal compounds, anilino heterocyclic fungicidal compounds, benzimidazole type fungicidal compounds and their precursors, sulfur, copper compounds, and carbamate type fungicidal compounds for controlling fungi tolerant to benzimidazole type fungicides.

The compounds of each type are further explained below.

The ethylenebis(dithiocarbamate) type fungicidal compounds include zinc salt (Zineb), manganese salt (Maneb), salt with zinc and manganese (Mancozeb), etc.

The N-(3,5-dichlorophenyl)imide type compounds include fungicidal compounds such as N-(3,5-dichlorophenyl)-1,2-dimethylcyclopropane-1,2-dicarboxyimide (Procymidone), 3-(3,5-dichlorophenyl)-5-methyl-5-vinyl-1,3-oxazolidine-2,4-dione (Vinclozolin) and 3-(3,5-dichlorophenyl)-N-(1-methylethyl)-2,4-dioxo-1-imidazolidinecarboxamide (Iprodione) which are fungicidal compounds having a partial structure represented by

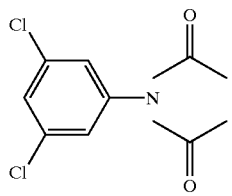

The phthalimide type compounds include, for example, N-(trichloromethylthio)phthalimide (Folpet) which is a compound having an N-substituted phthalimide structure, and 1,2,3,6-tetrahydro-N-(trichloromethylthio) phthalimide (Captan) and 1,2,3,6-tetrahydro-N-(1,1,2,2-tetrachloroethylthio)phthalimide (Captafol) which are compounds having an N-substituted tetrahydro-phthalimide structure.

The anilide type fungicidal compounds include compounds having a 2,6-dimethylanilide structure, such as methyl N-(2,6-dimethylphenyl)-N-(methoxyacetyl)-alaninate (Metalaxyl), methyl N-(2,6-dimethylphenyl)-N-(phenylacetyl) alaninate (Benalaxyl), methyl N-(2,6-dimethylphenyl)-N-(2-furanylcarbonyl)alaninate (Furalaxyl), 2-chloro-N-(2,6-dimethylphenyl)-N-(tetrahydro-2-oxo-3-furanyl)acetamide (Ofurace) and 2-methoxy-N-(2-oxo-1,3-oxazolidin-3-yl)aceto-2',6'-xylidide (Oxadixyl); and compounds having a 3-chloroanilide structure, such as N-(3-chlorophenyl)-N-(tetrahydro-2-oxo-3-furanyl)cyclopropanecarboxamide (Cyprofuram).

In addition to them, there are used 2-cyano-N-[ethylaminocarbonyl]-2-(methoxyimino)acetamide (Cymoxanil) and ethyl hydrogenphosphonate (Fosetyl) or its aluminum salt, etc.

The fungicidal composition comprising the anilide type fungicidal compound, Cymoxanil or Fosetyl and the compound of the formula I is markedly effective against various plant diseases and is particularly suitably used for controlling, among these diseases, downy mildew and late blight or Phytophthora rot of cucumber, grape and potato and plant diseases caused by fungi of the genus *Pythium*.

The cyanopyrrole type fungicidal compounds include compounds having a 4-aryl-1H-pyrrole-3-carbonitrile structure, such as 4-(2,2-difluoro-1,3-benzodioxol-4-yl)-1H-pyrrole-3-carbonitrile (Fludioxonil).

The anilino heterocyclic fungicidal compounds include, for example, compounds having a 2-anilino-pyrimidine structure, such as 2-anilino-4,6-dimethyl-pyrimidine (Pyrimetanil) and 2-anilino-4-methyl-6-(1-propynyl) pyrimidine (Mepanipyrim); and compounds having an N-aryl-2,6-dinitroaniline structure, such as 3-chloro-N-(3-chloro-5-trifluoromethyl-2-pyridyl)-α, α,α-trifluoro-2,6-dinitro-p-toluidine (Fluazinam).

The present fungicidal composition comprising any of these cyanopyrrole type fungicidal compounds or anilino heterocyclic fungicidal compounds is suitably used for controlling gray mold (*Botrytis cinerea*).

The benzimidazole type fungicidal compounds include methyl 1-(butylcarbamoyl)-2-benzimidazole-carbamate (Benomyl), benzimidazole-2-yl carbamate (Carbendazim) and 2-(4'-thiazolyl)benzimidazole (Thiabendazole). The precursors thereof include 1,2-bis(3-ethoxycarbonyl-2- thioureido)benzene (Thiophanate) and 1,2-bis(3-methoxycarbonyl-2-thioureido)benzene (Thiophanate-methyl) which are considered to be convertible into benzimidazol-2-yl carbamate in a plant.

The copper compounds includes various inorganic salts such as chloride, oxychloride, carbonate, oxide, hydroxide, sulfate, phosphate, silicate, zinc chromate, hydrazinium sulfate, etc., and organic salts such as acetate, copper oxyquinolinolate (8-hydroxyquinolinate), oxalate, bis(3-phenylsalicylate), naphthenate, linolenate, oleate, etc.

The carbamate type fungicidal compounds for controlling fungi tolerant to benzimidazole type fungicides refer to the 3,4-substituted, 3,5-substituted or 3,4,5-substituted N-phenylcarbamate compounds disclosed in Japanese Patent Unexamined Publication No. 57-171951, Japanese Patent Examined Publication Nos. 58-39802 and 4-39458, etc. More specifically, they refer to, for example, lower (number of carbon atoms: for instance, 1 to 4) alkyl phenylcarbamate compounds having substituents such as lower (number of carbon atoms: for instance, 1 to 4) alkoxy groups, lower (number of carbon atoms: for instance, 1 to 4) alkyl groups or halogen atoms at the 3- and 4-positions, 3- and 5-positions or 3-, 4- and 5-positions of the phenyl group, which are represented by Diethofencarb (isopropyl 3,4-diethoxy-phenylcarbamate).

When used in a fungicidal composition, the above-mentioned carbamate type fungicidal compounds for controlling fungi tolerant to benzimidazole type fungicides are very effective in controlling not only the fungi tolerant to the benzimidazole type fungicides but also fungi sensitive to the benzimidazole type fungicides.

Plant diseases that can be controlled by the composition of the present invention includes blast (*Pyricularia oryzae*), *helminthosporium* leaf spot (*Cochliobolus miyabeanus*) and sheath blight (*Rhizoctonia solani*) of rice; powdery mildew (*Erysiphe graminis* f. sp. *hordei*, f. sp. *tritici*), scab (*Gibberella zeae*), rust (*Puccinia striiformis, P. graminis, P. recondita, P. hordei*), snow blight (*Typhula* sp., *Micronectriella nivalis*), loose smut (*Ustilago tritici, U. nuda*), bunt (*Tilletia caries*), eye spot (*Pseudocercosporella herpotrichoides*), foot rot (*Rhizoctonia cerealis*), scald (*Rhynchosporium secalis*), leaf blight (*Septoria tritici*) and glume blotch (*Leptosphaeria nodorum*) of barley, wheat, oats and rye; melanose (*Diaporthe citri*), scab (*Elsinoe fawcetti*), *penicillium* rot (*Penicillium digitatum, P. italicum*) of citrus; blossom blight (*Sclerotinia mali*), canker (*Valsa mali*), powdery mildew (*Podosphaera leucotricha*), *Alternaria* leaf spot (*Alternaria mali*) and scab (*Venturia inaequalis*) of apple; scab (*Venturia nashicola*), black spot (*Alternaria kikuchiana*) and rust (*Gymnosporangium haraeanum*) of pear; brown rot (*Sclerotinia cinerea*), scab (*Cladosporium carpophilum*) and *Phomopsis* rot (*Phomopsis* sp.) of peach; downy mildew (*Plasmopara viticola*), *Sphaceloma* scab (*Elsinoe ampelina*), ripe rot (*Glomerellacing ulata*), powdery mildew (*Uncinula necator*) and rust (*Phakopora ampelopsidis*) of grape; anthracnose (*Gloeosporium kaki*) and leaf spot (*Cercospora kaki, Mycosphaerella nawae*) of Japanese persimmon; cucumber downy mildew (*Pseudoperonospora cubensis*); anthracnose (*Colletotrichum lagenarium*), powdery mildew (*Sphaerotheca fuliginea*) and gummy stem blight (*Mycosphaerella melonis*) of melons and cucumbers; early blight (*Alternaria solani*), leaf mold (*Cladosporium fulvum*) and late blight (*Phytophthora infestans*) of tomato; brown spot (*Phomopsis vexans*) and powdery mildew (*Erysiphe cichoracearum*) of eggplant; leaf spot (*Alternaria brassicae*) and white spot (*Cercosporella brassicae*) of vegetables of *Cruciferae*; onion rust (*Puccinia allii*); purple stain (*Cercospora kikuchii*), *Sphaceloma* scab (*Elisinoe glycines*) and pod and stem blight (*Diaporthe phaseolorum* var. *sajae*) of soybean; kidney bean anthracnose (*Colletotrichum lindemthianum*); leaf spot (*Mycosphaerella personatum*) and leaf spot (*Cercospora arachidicola*) of peanut; powdery mildew (*Erysiphe pisi*) and downy mildew (*Peronospora pisi*) of pea; downy mildew (*Peronospora viciae*) and *Phytophthora* rot (*Phytophthora nicotianae*) of broad bean; early blight (*Alternaria solani*) and late blight (*Phytophthora infestans*) of potato; powdery mildew (*Sphaerotheca humuli*) and *Phytophthora* rot (*Phytophthora nicotianae*) of strawberry; net blister blight (*Exobasidium recticulatum*) and white scab (*Erysiphe leucospila*) of tea plant; brown spot (*Alternaria longipes*), powdery mildew (*Erysiphe cichoracearum*), anthracnose (*Colletotrichum tabacum*) and *Phytophthora* rot (*Phytophthora parasitica*) of tobacco; beet leaf spot (*Cercospora beticola*); black spot (*Diplocarpon rosae*), powdery mildew (*Sphaerotheca pannosa*) and *Phytophthora* rot (*Phytophthora megasperma*) of rose; leaf spot (*Septoria chrysanthemlla*) and white rust (*Puccinia horiana*) of chrysanthemum; gray mold (*Botrytis cinerea*) and stem rot (*Sclerotinia sclerotiorum*) of fruit trees such as grape and citrus and various crops such as cucumber, tomato, beans and vegetables; and plant diseases caused by *Pythium* fungi (*Pythium* sp.).

In the fungicidal composition of the present invention, although the mixing proportions of the compound of the formula I used as active ingredient and the other active ingredient(s) selected from the group of compounds (b) are not particularly limited, the mixing may be carried out so as to adjust the amount of the compound of the formula I mixed with each of the other active ingredient(s) as follows.

Next, the weight of the at least one compound selected from the group (b) and mixed with 1 part by weight of the compound of the formula I is described below.

The proportion of the ethylenebis(dithiocarbamate) compound(s) ranges usually from 0.01 to 100 parts by weight, preferably from 0.1 to 50 parts by weight, more preferably from 1 to 20 parts by weight, per part by weight of the compound of the formula I.

The mixing proportion of the N-(3,5-dichlorophenyl) imide type compound(s) is usually 0.01 to 100 parts by weight, preferably 0.1 to 50 parts by weight.

The mixing proportion of Chlorothalonil is usually 0.1 to 10000 parts by weight, preferably 1 to 1000 parts by weight.

The mixing proportion of the phthalimide type fungicidal compound(s) is usually 0.1 to 10000 parts by weight, preferably 1 to 1000 parts by weight.

The using amount of at least one compound selected from the anilide type fungicidal compounds, Cymoxanil and Fosetyl is usually 0.001 to 100 parts by weight, preferably 0.1 to 50 parts by weight.

The using amount of the cyanopyrrole type fungicidal compound(s) or anilino heterocyclic fungicidal compound (s) is usually 0.001 to 100 parts by weight, preferably 0.002 to 20 parts by weight.

The using amount of the benzimidazole type fungicidal compound(s) or precursor(s) thereof is usually 0.01 to 100 parts by weight, preferably 0.02 to 50 parts by weight.

The using amount of sulfur is usually 1 to 5000 parts by weight, preferably 5 to 1000 parts by weight.

The using amount of the copper compound(s) is usually 0.01 to 1000 parts by weight, preferably 0.1 to 100 parts by weight.

The using amount of the carbamate type fungicidal compound(s) ranges usually from 0.01 to 100 parts by weight, preferably from 0.02 to 50 parts by weight.

The fungicidal composition of the present invention is applied usually after being formulated into an emulsifiable concentrate, wettable powder, suspension, granules, dust, dry flowable concentrate, aqueous soluble concentrate, oil formulation, smoking formulation, aerosol, microcapsules or the like, by mixing with a solid carrier, liquid carrier or gaseous carrier and optionally addition of adjuncts for formulation such as surfactants, fixing agents, dispersants, stabilizers, etc.

The compounds as active ingredients are usually contained in such a formulation in a total amount of 0.1 to 99% by weight, preferably 0.2 to 90% by weight.

The solid carrier includes, for example, fine powders or granules of clays (e.g. kaolin clay, diatomaceous earth, synthetic hydrated silicon dioxide, attapulgite clay, bentonite and acid clay), talcs, other inorganic minerals (e.g. sericite, powdered quartz, powdered sulfur, activated carbon, calcium carbonate and hydrated silica), and salts for chemical fertilizers (e.g. ammonium sulfate, ammonium phosphate, ammonium nitrate, urea and ammonium chloride). The liquid carrier includes, for example, water, alcohols (e.g. methanol and ethanol), ketones (e.g. acetone, methyl ethyl ketone and cyclohexanone), aromatic hydrocarbons (e.g. benzene, toluene, xylene, ethylbenzene and methylnaphthalene), aliphatic hydrocarbons (e.g. hexane and kerosene), esters (e.g. ethyl acetate and butyl acetate), nitriles (e.g. acetonitrile and isobutyronitrile), ethers (e.g. dioxane and diisopropyl ether), acid amides (e.g. dimethylformamide and dimethylacetamide), and halogenated hydrocarbons (e.g. dichloroethane, trichloroethylene and carbon tetrachloride). The gaseous carrier includes butane gas, carbon dioxide, fluorocarbon gas, etc.

The surfactants include alkyl sulfates, alkylsulfonates, alkylarylsulfonates, alkyl aryl ethers and their polyoxyethylenated products, polyethylene glycol ethers, polyhydric alcohol esters, sugar alcohol derivatives, etc.

The fixing agents and dispersants include casein, gelatin, polysaccharides (e.g. starch, gum arabic, cellulose derivatives and alginic acid), lignin derivatives, bentonite, saccharides, synthetic water-soluble polymers [e.g. poly(vinyl alcohol)s, poly(vinyl-pyrrolidone)s and poly(acrylic acid)s], etc. The stabilizers include PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or their esters, etc.

The above-mentioned formulations are applied to plants or soil as they are or after being diluted with water or the like. When applied to soil, they may be sprinkled on the soil surface or mixed with the soil. They may be applied also by any of various methods such as seed treatment, ULV, etc.

When used as a seed-treating agent, the formulations are used by dressing of seeds, seed immersion or the like.

In addition, the formulations may be used in combination with other fungicides, insecticides, acaricides, nematicides, herbicides, seed disinfectants, fertilizers, soil conditioners, etc.

Although the applying dosage of the fungicidal composition of the present invention is varied depending on the kinds of the compounds used as active ingredients; their mixing proportions; weather conditions; type of formulation; application time, method and site; diseases to be controlled; a crop to be protected; and the like, it is usually 0.001 to 1000 g, preferably 0.1 to 100 g, per are. When the emulsifiable concentrate, wettable powder, suspension, soluble concentrate or the like is used after being diluted with water, the applying concentration thereof is 0.0001 to 1% by weight, preferably 0.001 to 0.5% by weight. The granules, dust and the like are used as they are without dilution.

For seed treatment, the fungicidal composition is used in an amount of usually 0.001 to 50 g, preferably 0.01 to 10 g, (in terms of the sum of the compounds used as active ingredients) per kg of seeds.

EXAMPLES

The present invention is explained below in further detail with formulation examples and test examples, but the present invention is not limited to the following examples. In the following examples, parts and percents are all by weight unless otherwise specified.

Formulation Example 1

Granules are obtained by thoroughly grinding and mixing 1 part of compound (Ia), (Ib), (Ic), (Id), (Ie), (If) or (Ig), 5 parts of an ethylenebis(dithiocarbamate) compound, 1 part of synthetic hydrated silicon dioxide, 2 parts of calcium lignin sulfonate, 30 parts of bentonite and 61 parts of kaolin clay, and thoroughly kneading the resulting mixture together with water, followed by granulation and drying.

Formulation Example 2

Granules are obtained by thoroughly grinding and mixing 5 parts of compound (Ia), (Ib), (Ic), (Id), (Ie), (If) or (Ig), 5 parts of an ethylenebis(dithiocarbamate) compound, 1 part of synthetic hydrated silicon dioxide, 2 parts of calcium lignin sulfonate, 30 parts of bentonite and 57 parts of kaolin clay, and thorougly kneading the resulting mixture together with water, followed by granulation and drying.

Formulation Example 3

A dust is obtained by thoroughly grinding and mixing 0.5 part of compound (Ia), (Ib), (Ic), (Id), (Ie), (If) or (Ig), 2.5 parts of an ethylenebis(dithiocarbamate) compound, 86 parts of kaolin clay and 11 parts of talc.

Formulation Example 4

A suspension is obtained by mixing 5 parts of compound (Ia), (Ib), (Ic), (Id), (Ie), (If) or (Ig), 25 parts of an ethylenebis(dithiocarbamate) compound, 3 parts of polyoxyethylene sorbitan monooleate, 3 parts of carboxymethyl cellulose and 64 parts of water, followed by wet grinding to a particle size of 5 microns or less.

Formulation Example 5

A wettable powder is obtained by thoroughly grinding and mixing 10 parts of compound (Ia), (Ib), (Ic), (Id), (Ie), (If) or (Ig), 50 parts of an ethylene-bis(dithiocarbamate) compound, 3 parts of calcium lignin sulfonate, 2 parts of sodium lauryl sulfate and 35 parts of synthetic hydrated silicon dioxide.

Formulation Example 6

An emulsifiable concentrate is obtained by mixing 5 parts of compound (Ia), (Ib), (Ic), (Id), (Ie), (If) or (Ig), 25 parts of an ethylenebis(dithiocarbamate) compound, 14 parts of polyoxyethylene styrylphenyl ether, 6 parts of calcium dodecylbenzene-sulfonate and 50 parts of xylene.

Formulation Example 7

Granules are obtained by thoroughly grinding and mixing 1 part of compound (Ia), (Ib), (Ic), (Id), (Ie), (If) or (Ig), 5 parts of Procymidone, Vinclozolin or Iprodione, 1 part of synthetic hydrated silicon dioxide, 2 parts of calcium lignin sulfonate, 30 parts of bentonite and 61 parts of kaolin clay, and thoroughly kneading the resulting mixture together with water, followed by granulation and drying.

Formulation Example 8

Granules are obtained by thoroughly grinding and mixing 5 parts of compound (Ia), (Ib), (Ic), (Id), (Ie), (If) or (Ig), 5 parts of Procymidone, Vinclozolin or Iprodione, 1 part of synthetic hydrated silicon dioxide, 2 parts of calcium lignin sulfonate, 30 parts of bentonite and 57 parts of kaolin clay, and thoroughly kneading the resulting mixture together with water, followed by granulation and drying.

Formulation Example 9

A dust is obtained by thoroughly grinding and mixing 0.5 part of compound (Ia), (Ib), (Ic), (Id), (Ie), (If) or (Ig), 2.5 parts of Procymidone, Vinclozolin or Iprodione, 86 parts of kaolin clay and 11 parts of talc.

Formulation Example 10

A suspension is obtained by mixing 5 parts of compound (Ia), (Ib), (Ic), (Id), (Ie), (If) or (Ig), 25 parts of Procymidone, Vinclozolin or Iprodione, 3 parts of polyoxyethylene sorbitan monooleate, 3 parts of carboxymethyl cellulose and 64 parts of water, followed by wet grinding to a particle size of 5 microns or less.

Formulation Example 11

A wettable powder is obtained by thoroughly grinding and mixing 10 parts of compound (Ia), (Ib), (Ic), (Id), (Ie), (If) or (Ig), 50 parts of Procymidone, Vinclozolin or Iprodione, 3 parts of calcium lignin sulfonate, 2 parts of sodium lauryl sulfate and 35 parts of synthetic hydrated silicon dioxide.

Formulation Example 12

An emulsifiable concentrate is obtained by mixing 5 parts of compound (Ia), (Ib), (Ic), (Id), (Ie), (If) or (Ig), 25 parts of Procymidone, Vinclozolin or Iprodione, 14 parts of polyoxyethylene styrylphenyl ether, 6 parts of calcium dodecylbenzenesulfonate and 50 parts of xylene.

Formulation Example 13

Granules are obtained by thoroughly grinding and mixing 1 part of compound (Ia), (Ib), (Ic), (Id), (Ie), (If) or (Ig), 5 parts of Chlorothalonil, 1 part of synthetic hydrated silicon dioxide, 2 parts of calcium lignin sulfonate, 30 parts of bentonite and 61 parts of kaolin clay, and thoroughly kneading the resulting mixture together with water, followed by granulation and drying.

Formulation Example 14

Granules are obtained by thoroughly grinding and mixing 5 parts of compound (Ia), (Ib), (Ic), (Id), (Ie), (If) or (Ig), 5 parts of Chlorothalonil compound, 1 part of synthetic hydrated silicon dioxide, 2 parts of calcium lignin sulfonate, 30 parts of bentonite and 57 parts of kaolin clay, and thoroughly kneading the resulting mixture together with water, followed by granulation and drying.

Formulation Example 15

A dust is obtained by thoroughly grinding and mixing 0.5 part of compound (Ia), (Ib), (Ic), (Id), (Ie), (If) or (Ig), 2.5 parts of Chlorothalonil, 86 parts of kaolin clay and 11 parts of talc.

Formulation Example 16

A suspension is obtained by mixing 5 parts of compound (Ia), (Ib), (Ic), (Id), (Ie), (If) or (Ig), 25 parts of Chlorothalonil, 3 parts of polyoxyethylene sorbitan monooleate, 3 parts of carboxymethyl cellulose and 64 parts of water, followed by wet grinding to a particle size of 5 microns or less.

Formulation Example 17

A wettable powder is obtained by thoroughly grinding and mixing 10 parts of compound (Ia), (Ib), (Ic), (Id), (Ie), (If) or (Ig), 50 parts of Chlorolothanil, 3 parts of calcium lignin sulfonate, 2 parts of sodium lauryl sulfate and 35 parts of synthetic hydrated silicon dioxide.

Formulation Example 18

An emulsifiable concentrate is obtained by mixing 5 parts of compound (Ia), (Ib), (Ic), (Id), (Ie), (If) or (Ig), 25 parts of Chlorothalonil compound, 14 parts of polyoxyethylene styrylphenyl ether, 6 parts of calcium dodecylbenzenesulfonate and 50 parts of xylene.

Formulation Example 19

Granules are obtained by thoroughly grinding and mixing 1 part of compound (Ia), (Ib), (Ic), (Id), (Ie), (If) or (Ig), 5 parts of a phthalimide type fungicidal compound, 1 part of synthetic hydrated silicon dioxide, 2 parts of calcium lignin sulfonate, 30 parts of bentonite and 61 parts of kaolin clay, and thoroughly kneading the resulting mixture together with water, followed by granulation and drying.

Formulation Example 20

Granules are obtained by thoroughly grinding and mixing 5 parts of compound (Ia), (Ib), (Ic), (Id), (Ie), (If) or (Ig), 5 parts of a phthalimide type fungicidal compound, 1 part of synthetic hydrated silicon dioxide, 2 parts of calcium lignin sulfonate, 30 parts of bentonite and 57 parts of kaolin clay, and thoroughly kneading the resulting mixture together with water, followed by granulation and drying.

Formulation Example 21

A dust is obtained by thoroughly grinding and mixing 0.5 part of compound (Ia), (Ib), (Ic), (Id), (Ie), (If) or (Ig), 2.5 parts of a phthalimide type fungicidal compound, 86 parts of kaolin clay and 11 parts of talc.

Formulation Example 22

A suspension is obtained by mixing 5 parts of compound (Ia), (Ib), (Ic), (Id), (Ie), (If) or (Ig), 25 parts of a phthalimide type fungicidal compound, 3 parts of polyoxyethylene sorbitan monooleate, 3 parts of carboxymethyl cellulose and 64 parts of water, followed by wet grinding to a particle size of 5 microns or less.

Formulation Example 23

A wettable powder is obtained by thoroughly grinding and mixing 10 parts of compound (Ia), (Ib), (Ic), (Id), (Ie), (If) or (Ig), 50 parts of a phthalimide type fungicidal compound, 3 parts of calcium lignin sulfonate, 2 parts of sodium lauryl sulfate and 35 parts of synthetic hydrated silicon dioxide.

Formulation Example 24

An emulsifiable concentrate is obtained by mixing 5 parts of compound (Ia), (Ib), (Ic), (Id), (Ie), (If) or (Ig), 25 parts of a phthalimide type fungicidal compound, 14 parts of polyoxyethylene styrylphenyl ether, 6 parts of calcium dodecylbenzenesulfonate and 50 parts of xylene.

Formulation Example 25

Granules are obtained by thoroughly grinding and mixing 1 part of compound (Ia), (Ib), (Ic), (Id), (Ie), (If) or (Ig), 5 parts of an anilide type fungicidal compound, Cymoxanil or Fosetyl aluminum, 1 part of synthetic hydrated silicon dioxide, 2 parts of calcium lignin sulfonate, 30 parts of bentonite and 61 parts of kaolin clay, and thoroughly kneading the resulting mixture together with water, followed by granulation and drying.

Formulation Example 26

Granules are obtained by thoroughly grinding and mixing 5 parts of compound (Ia), (Ib), (Ic), (Id), (Ie), (If) or (Ig), 5 parts of an anilide type fungicidal compound, Cymoxanil or Fosetyl aluminum, 1 part of synthetic hydrated silicon dioxide, 2 parts of calcium lignin sulfonate, 30 parts of bentonite and 57 parts of kaolin clay, and thoroughly kneading the resulting mixture together with water, followed by granulation and drying.

Formulation Example 27

A dust is obtained by thoroughly grinding and mixing 0.5 part of compound (Ia), (Ib), (Ic), (Id), (Ie), (If) or (Ig), 2.5 parts of an anilide type fungicidal compound, Cymoxanil or Fosetyl aluminum, 86 parts of kaolin clay and 11 parts of talc.

Formulation Example 28

A suspension is obtained by mixing 5 parts of compound (Ia), (Ib), (Ic), (Id), (Ie), (If) or (Ig), 25 parts of an anilide type fungicidal compound, Cymoxanil or Fosetyl aluminum, 3 parts of polyoxyethylene sorbitan monooleate, 3 parts of carboxymethyl cellulose and 64 parts of water, followed by wet grinding to a particle size of 5 microns or less.

Formulation Example 29

A wettable powder is obtained by thoroughly grinding and mixing 10 parts of compound (Ia), (Ib), (Ic), (Id), (Ie), (If) or (Ig), 50 parts of an anilide type fungicidal compound, Cymoxanil or Fosetyl aluminum, 3 parts of calcium lignin sulfonate, 2 parts of sodium lauryl sulfate and 35 parts of synthetic hydrated silicon dioxide.

Formulation Example 30

An emulsifiable concentrate is obtained by mixing 5 parts of compound (Ia), (Ib), (Ic), (Id), (Ie), (If) or (Ig), 25 parts of an anilide type fungicidal compound, Cymoxanil or Fosetyl aluminum, 14 parts of polyoxyethylene styrylphenyl ether, 6 parts of calcium dodecylbenzenesulfonate and 50 parts of xylene.

Formulation Example 31

Granules are obtained by thoroughly grinding and mixing 1 part of compound (Ia), (Ib), (Ic), (Id), (Ie), (If) or (Ig), 5 parts of Fludioxonil, Pyrimetanil, Mepanipyrim or Fluazinam, 1 part of synthetic hydrated silicon dioxide, 2 parts of calcium lignin sulfonate, 30 parts of bentonite and 61 parts of kaolin clay, and thoroughly kneading the resulting mixture together with water, followed by granulation and drying.

Formulation Example 32

Granules are obtained by thoroughly grinding and mixing 5 parts of compound (Ia), (Ib), (Ic), (Id), (Ie), (If) or (Ig), 5 parts of Fludioxonil, Pyrimetanil, Mepanipyrim or Fluazinam, 1 part of synthetic hydrated silicon dioxide, 2 parts of calcium lignin sulfonate, 30 parts of bentonite and 57 parts of kaolin clay, and thoroughly kneading the resulting mixture together with water, followed by granulation and drying.

Formulation Example 33

A dust is obtained by thoroughly grinding and mixing 0.5 part of compound (Ia), (Ib), (Ic), (Id), (Ie), (If) or (Ig), 2.5 parts of Fludioxonil, Pyrimetanil, Mepanipyrim or Fluazinam, 86 parts of kaolin clay and 11 parts of talc.

Formulation Example 34

A suspension is obtained by mixing 5 parts of compound (Ia), (Ib), (Ic), (Id), (Ie), (If) or (Ig), 25 parts of Fludioxonil, Pyrimetanil, Mepanipyrim or Fluazinam, 3 parts of polyoxyethylene sorbitan monooleate, 3 parts of carboxymethyl cellulose and 64 parts of water, followed by wet grinding to a particle size of 5 microns or less.

Formulation Example 35

A wettable powder is obtained by thoroughly grinding and mixing 10 parts of compound (Ia), (Ib), (Ic), (Id), (Ie), (If) or (Ig), 50 parts of Fludioxonil, Pyrimetanil, Mepanipyrim or Fluazinam, 3 parts of calcium lignin sulfonate, 2 parts of sodium lauryl sulfate and 35 parts of synthetic hydrated silicon dioxide.

Formulation Example 36

An emulsifiable concentrate is obtained by mixing 5 parts of compound (Ia), (Ib), (Ic), (Id), (Ie), (If) or (Ig), 25 parts of Fludioxonil, Pyrimetanil, Mepanipyrim or Fluazinam, 14 parts of polyoxyethylene styrylphenyl ether, 6 parts of calcium dodecylbenzene-sulfonate and 50 parts of xylene.

Formulation Example 37

Granules are obtained by thoroughly grinding and mixing 1 part of compound (Ia), (Ib), (Ic), (Id), (Ie), (If) or (Ig), 5 parts of Benomyl, Carbendazim, Thiabendazole, Thiophanate or Thiophanate-methyl, 1 part of synthetic hydrated silicon dioxide, 2 parts of calcium lignin sulfonate, 30 parts of bentonite and 61 parts of kaolin clay, and thoroughly kneading the resulting mixture together with water, followed by granulation and drying.

Formulation Example 38

Granules are obtained by thoroughly grinding and mixing 5 parts of compound (Ia), (Ib), (Ic), (Id), (Ie), (If) or (Ig), 5 parts of Benomyl, Carbendazim, Thiabendazole, Thiophanate or Thiophanate-methyl, 1 part of synthetic hydrated silicon dioxide, 2 parts of calcium lignin sulfonate, 30 parts of bentonite and 57 parts of kaolin clay, and thoroughly kneading the resulting mixture together with water, followed by granulation and drying.

Formulation Example 39

A dust is obtained by thoroughly grinding and mixing 0.5 part of compound (Ia), (Ib), (Ic), (Id), (Ie), (If) or (Ig), 2.5 parts of Benomyl, Carbendazim, Thiabendazole, Thiophanate or Thiophanate-methyl, 86 parts of kaolin clay and 11 parts of talc.

Formulation Example 40

A suspension is obtained by mixing 5 parts of compound (Ia), (Ib), (Ic), (Id), (Ie), (If) or (Ig), 25 parts of Benomyl, Carbendazim, Thiabendazole, Thiophanate or Thiophanate-methyl, 3 parts of polyoxyethylene sorbitan monooleate, 3 parts of carboxymethyl cellulose and 64 parts of water, followed by wet grinding to a particle size of 5 microns or less.

Formulation Example 41

A wettable powder is obtained by thoroughly grinding and mixing 10 parts of compound (Ia), (Ib), (Ic), (Ic), (Ie), (If) or (Ig), 50 parts of Benomyl, Carbendazim, Thiabendazole, Thiophanate or Thiophanate-methyl, 3 parts of calcium lignin sulfonate, 2 parts of sodium lauryl sulfate and 35 parts of synthetic hydrated silicon dioxide.

Formulation Example 42

An emulsifiable concentrate is obtained by mixing 5 parts of compound (Ia), (Ib), (Ic), (Id), (Ie), (If) or (Ig), 25 parts of Benomyl, Carbendazim, Thiabendazole, Thiophanate or Thiophanate-methyl, 14 parts of polyoxyethylene styrylphenyl ether, 6 parts of calcium dodecylbenzenesulfonate and 50 parts of xylene.

Formulation Example 43

Granules are obtained by thoroughly grinding and mixing 1 part of compound (Ia), (Ib), (Ic), (Id), (Ie), (If) or (Ig), 5 parts of sulfur, 1 part of synthetic hydrated silicon dioxide, 2 parts of calcium lignin sulfonate, 30 parts of bentonite and 61 parts of kaolin clay, and thoroughly kneading the resulting mixture together with water, followed by granulation and drying.

Formulation Example 44

Granules are obtained by thoroughly grinding and mixing 5 parts of compound (Ia), (Ib), (Ic), (Id), (Ie), (If) or (Ig), 5 parts of sulfur, 1 part of synthetic hydrated silicon dioxide, 2 parts of calcium lignin sulfonate, 30 parts of bentonite and 57 parts of kaolin clay, and thoroughly kneading the resulting mixture together with water, followed by granulation and drying.

Formulation Example 45

A dust is obtained by thoroughly grinding and mixing 0.5 part of compound (Ia), (Ib), (Ic), (Id), (Ie), (If) or (Ig), 2.5 parts of sulfur, 86 parts of kaolin clay and 11 parts of talc.

Formulation Example 46

A suspension is obtained by mixing 5 parts of compound (Ia), (Ib), (Ic), (Id), (Ie), (If) or (Ig), 25 parts of sulfur, 3 parts of polyoxyethylene sorbitan monooleate, 3 parts of carboxymethyl cellulose and 64 parts of water, followed by wet grinding to a particle size of 5 microns or less.

Formulation Example 47

A wettable powder is obtained by thoroughly grinding and mixing 10 parts of compound (Ia), (Ib), (Ic), (Id), (Ie), (If) or (Ig), 50 parts of sulfur, 3 parts of calcium lignin sulfonate, 2 parts of sodium lauryl sulfate and 35 parts of synthetic hydrated silicon dioxide.

Formulation Example 48

An emulsifiable concentrate is obtained by mixing 5 parts of compound (Ia), (Ib), (Ic), (Id), (Ie), (If) or (Ig), 25 parts of sulfur, 14 parts of polyoxyethylene styrylphenyl ether, 6 parts of calcium dodecylbenzenesulfonate and 50 parts of xylene.

Formulation Example 49

Granules are obtained by thoroughly grinding and mixing 1 part of compound (Ia), (Ib), (Ic), (Id), (Ie), (If) or (Ig), 5 parts of a copper compound, 1 part of synthetic hydrated silicon dioxide, 2 parts of calcium lignin sulfonate, 30 parts of bentonite and 61 parts of kaolin clay, and thoroughly kneading the resulting mixture together with water, followed by granulation and drying.

Formulation Example 50

Granules are obtained by thoroughly grinding and mixing 5 parts of compound (Ia), (Ib), (Ic), (Id), (Ie), (If) or (Ig), 5 parts of a copper compound, 1 part of synthetic hydrated silicon dioxide, 2 parts of calcium lignin sulfonate, 30 parts of bentonite and 57 parts of kaolin clay, and thoroughly kneading the resulting mixture together with water, followed by granulation and drying.

Formulation Example 51

A dust is obtained by thoroughly grinding and mixing 0.5 part of compound (Ia), (Ib), (Ic), (Id), (Ie), (If) or (Ig), 2.5 parts of a copper compound, 86 parts of kaolin clay and 11 parts of talc.

Formulation Example 52

A suspension is obtained by mixing 5 parts of compound (Ia), (Ib), (Ic), (Id), (Ie), (If) or (Ig), 25 parts of a copper compound, 3 parts of polyoxyethylene sorbitan monooleate, 3 parts of carboxymethyl cellulose and 64 parts of water, followed by wet grinding to a particle size of 5 microns or less.

Formulation Example 53

A wettable powder is obtained by thoroughly grinding and mixing 10 parts of compound (Ia), (Ib), (Ic), (Id), (Ie), (If) or (Ig), 50 parts of a copper compound, 3 parts of calcium lignin sulfonate, 2 parts of sodium lauryl sulfate and 35 parts of synthetic hydrated silicon dioxide.

Formulation Example 54

An emulsifiable concentrate is obtained by mixing 5 parts of compound (Ia), (Ib), (Ic), (Id), (Ie), (If) or (Ig), 25 parts of a copper compound, 14 parts of polyoxyethylene styrylphenyl ether, 6 parts of calcium dodecylbenzenesulfonate and 50 parts of xylene.

Formulation Example 55

Granules are obtained by thoroughly grinding and mixing 5 parts of Diethofencarb, 1 part of compound (Ia), (Ib), (Ic), (Id), (Ie), (If) or (Ig), 1 part of synthetic hydrated silicon dioxide, 2 parts of calcium lignin sulfonate, 30 parts of bentonite and 61 parts of kaolin clay, and thoroughly kneading the resulting mixture together with water, followed by granulation and drying.

Formulation Example 56

Granules are obtained by thoroughly grinding and mixing 5 parts of Diethofencarb, 5 parts of compound (Ia), (Ib), (Ic), (Id), (Ie), (If) or (Ig), 1 part of synthetic hydrated silicon dioxide, 2 parts of calcium lignin sulfonate, 30 parts of bentonite and 57 parts of kaolin clay, and thoroughly kneading the resulting mixture together with water, followed by granulation and drying.

Formulation Example 57

A dust is obtained by thoroughly grinding and mixing 2.5 parts of Diethofencarb compound, 0.5 part of compound (Ia), (Ib), (Ic), (Id), (Ie), (If) or (Ig), 86 parts of kaolin clay and 11 parts of talc.

Formulation Example 58

A suspension is obtained by mixing 25 parts of Diethofencarb compound, 5 parts of compound (Ia), (Ib), (Ic), (Id), (Ie), (If) or (Ig), 3 parts of polyoxyethylene sorbitan monooleate, 3 parts of carboxymethyl cellulose and 64 parts of water, followed by wet grinding to a particle size of 5 microns or less.

Formulation Example 59

A wettable powder is obtained by thoroughly grinding and mixing 50 parts of Diethofencarb, 10 parts of compound (Ia), (Ib), (Ic), (Id), (Ie), (If) or (Ig), 3 parts of calcium lignin sulfonate, 2 parts of sodium lauryl sulfate and 35 parts of synthetic hydrated silicon dioxide.

Formulation Example 60

An emulsifiable concentrate is obtained by mixing 25 parts of Diethofencarb, 5 parts of compound (Ia), (Ib), (Ic), (Id), (Ie), (If) or (Ig), 14 parts of polyoxyethylene styrylphenyl ether, 6 parts of calcium dodecylbenzenesulfonate and 50 parts of xylene.

Test Example 1

A tomato plant (cultivar: Ponterosa) was planted in each pot and was sprayed with a sufficient volume of a dilution with a predetermined concentration of a wettable powder obtained according to Formulation Example 5, after the plant put out a third leaf. After air-drying of the liquid chemical, the surfaces of the leaves were inoculated with a suspension of spores ($5 \times 10^4$ spores/ml) of tomato late blight fungus (*Phytophthora infestans*) by spraying. The plant was grown at 24° C. for 1 week, after which the infection rate (%) was investigated.

The results are shown in Table 1.

TABLE 1

| Agent tested | Amount of agent applied (ppm) | Infection rate (%) |
| --- | --- | --- |
| Compound (Ia) | 10 | 25 |
| Compound (Ib) | 50 | 25 |
| Compound (Ic) | 10 | 25 |
| Compound (Id) | 10 | 25 |
| Compound (Ie) | 10 | 25 |
| Mancozeb | 50 | 25 |
| Compound (Ia) + Mancozeb | 10 + 50 | 0 |
| Compound (Ib) + Mancozeb | 50 + 50 | 0 |
| Compound (Ic) + Mancozeb | 10 + 50 | 0 |
| Compound (Id) + Mancozeb | 10 + 50 | 0 |
| Compound (Ie) + Mancozeb | 10 + 50 | 0 |

Test Example 2

A grape plant (cultivar: Berry A) was planted in each pot and was sprayed with a sufficient volume of a dilution with a predetermined concentration of a wettable powder obtained according to Formulation Example 5, after the plant put out a fourth leaf. After air-drying of the liquid chemical, the surfaces of the leaves were inoculated with a suspension of spores (2×105 spores/ml) of grape downy mildew fungus (*Plasmopara viticola*) by spraying. The plant was grown at 24° C. for 1 week, after which the infection rate (%) was investigated.

The results are shown in Table 2.

TABLE 2

| Agent tested | Amount of agent applied (ppm) | Infection rate (%) |
| --- | --- | --- |
| Compound (Ia) | 10 | 30 |
| Compound (Ib) | 50 | 25 |
| Compound (Ic) | 10 | 25 |
| Compound (Id) | 10 | 25 |
| Compound (Ie) | 10 | 25 |
| Mancozeb | 50 | 25 |
| Compound (Ia) + Mancozeb | 10 + 50 | 0 |
| Compound (Ib) + Mancozeb | 50 + 50 | 0 |
| Compound (Ic) + Mancozeb | 10 + 50 | 0 |
| Compound (Id) + Mancozeb | 10 + 50 | 0 |
| Compound (Ie) + Mancozeb | 10 + 50 | 0 |

Test Example 3

Each of plastic pots was filled with sandy loam and sown with cucumber (Sagamihanjiro), followed by growing in a greenhouse for 14 days. A wettable powder of test agents prepared according to Formulation Example 11 was diluted to a predetermined concentration with water, and foliage application of the dilution was carried out so as to adhere the dilution sufficiently to the surfaces of leaves of the grown cucumber young seedling. After air-drying, gray mold fungus was inoculated on the surfaces of leaves of the young seedling, and the young seedling was grown in the dark at 10° C. and a high humidity for 4 days, after which the infection rate (%) was investigated.

The results are shown in Table 3.

TABLE 3

| Agent tested | Amount of agent applied (ppm) | Infection rate (%) |
| --- | --- | --- |
| Compound (Ia) | 10 | 30 |
| Compound (Ib) | 200 | 20 |
| Compound (Ic) | 200 | 20 |
| Compound (Id) | 200 | 20 |
| Compound (Ie) | 20 | 25 |
| Procymidone | 10 | 25 |
| Compound (Ia) + Procymidone | 10 + 10 | 0 |
| Compound (Ib) + Procymidone | 200 + 10 | 0 |
| Compound (Ic) + Procymidone | 200 + 10 | 0 |
| Compound (Id) + Procymidone | 200 + 10 | 0 |
| Compound (Ie) + Procymidone | 20 + 10 | 0 |

Test Example 4

Each of plastic pots was filled with sandy loam and sown with cucumber (Sagamihanjiro), followed by growing in a greenhouse for 14 days. Gray mold fungus was inoculated on the surfaces of leaves of the grown cucumber young seedling, and the young seedling was grown in the dark at 10° C. and a high humidity for 2 days and then at a temperature of 23° C. for 3 days. A wettable powder of test agents prepared according to Formulation Example 11 was diluted to a predetermined concentration with water, and foliage application of the dilution was carried out so as to adhere the dilution sufficiently to the surfaces of leaves of the cucumber young seedling. After the spraying, the young seedling was grown in the dark at 10° C. and a high humidity for 3 days, and then the infection rate (%) was investigated.

The results are shown in Table 4.

TABLE 4

| Agent tested | Amount of agent applied (ppm) | Infection rate (%) |
| --- | --- | --- |
| Compound (Ia) | 10 | 30 |
| Compound (Ib) | 200 | 20 |
| Compound (Ic) | 200 | 20 |
| Compound (Id) | 200 | 20 |
| Compound (Ie) | 20 | 25 |
| Procymidone | 10 | 25 |
| Compound (Ia) + Procymidone | 10 + 10 | 0 |
| Compound (Ib) + Procymidone | 200 + 10 | 0 |
| Compound (Ic) + Procymidone | 200 + 10 | 0 |
| Compound (Id) + Procymidone | 200 + 10 | 0 |
| Compound (Ie) + Procymidone | 20 + 10 | 0 |

Test Example 5

Each of plastic pots was filled with sandy loam and sown with tomato (Ponterosa), followed by growing in a greenhouse for 20 days. A wettable powder of test agents prepared according to Formulation Example 17 was diluted to a predetermined concentration with water, and foliage application of the dilution was carried out so as to adhere the dilution sufficiently to the surfaces of leaves of the tomato young seedling which had put out two true leaves. Then, the young seedling was inoculated with a suspension of zoosporangia of tomato late blight fungus by spraying. After the inoculation, the young seedling was allowed to stand overnight at 23° C. and a high humidity and then grown in a greenhouse for 4 days, after which the infection rate (%) was investigated.

The results are shown in Table 5.

TABLE 5

| Agent tested | Amount of agent applied (ppm) | Infection rate (%) |
| --- | --- | --- |
| Compound (Ia) | 50 | 25 |
| Compound (Ib) | 40 | 20 |
| Compound (Ic) | 40 | 20 |
| Compound (Id) | 40 | 20 |
| Compound (Ie) | 10 | 20 |
| Chlorothalonil | 40 | 20 |
| Compound (Ia) + Chlorothalonil | 50 + 40 | 0 |
| Compound (Ib) + Chlorothalonil | 40 + 40 | 0 |
| Compound (Ic) + Chlorothalonil | 40 + 40 | 0 |
| Compound (Id) + Chlorothalonil | 40 + 40 | 0 |
| Compound (Ie) + Chlorothalonil | 10 + 40 | 0 |

Test Example 6

Each of plastic pots was filled with sandy loam and sown with grape (Berry A), followed by growing in a greenhouse for 40 days. A suspension of test agents prepared according to Formulation Example 16 were diluted to a predetermined concentration with water, and foliage application of the dilution was carried out so as to adhere the dilution sufficiently to the surfaces of leaves of the grape young seedling which had put out three true leaves. Then, the young seedling was inoculated with a suspension of zoosporangia of grape downy mildew fungus by spraying. After the inoculation, the young seedling was allowed to stand overnight at 23° C. and a high humidity and then grown in a greenhouse for 7 days, after which the infection rate (%) was investigated.

The results are shown in Table 6.

TABLE 6

| Agent tested | Amount of agent applied (ppm) | Infection rate (%) |
| --- | --- | --- |
| Compound (Ia) | 5 | 20 |
| Compound (Ib) | 5 | 20 |
| Compound (Ic) | 5 | 25 |
| Compound (Id) | 5 | 25 |
| Compound (Ie) | 1 | 25 |
| Chlorothalonil | 30 | 20 |
| Compound (Ia) + Chlorothalonil | 5 + 30 | 0 |
| Compound (Ib) + Chlorothalonil | 5 + 30 | 0 |
| Compound (Ic) + Chlorothalonil | 5 + 30 | 0 |
| Compound (Id) + Chlorothalonil | 5 + 30 | 0 |
| Compound (Ie) + Chlorothalonil | 1 + 30 | 0 |

Test Example 7

Each of plastic pots was filled with sandy loam and sown with grape (Berry A), followed by growing in a greenhouse for 40 days. A wettable powder prepared of test agents according to Formulation Example 23 was diluted to a predetermined concentration with water, and foliage application of the dilution was carried out so as to adhere the dilution sufficiently to the surfaces of leaves of the grape young seedling which had put out three true leaves. Then, the young seedling was inoculated with a suspension of zoosporangia of grape downy mildew fungus by spraying. After the inoculation, the young seedling was allowed to stand overnight at 23° C. and a high humidity and then grown in a greenhouse for 7 days, after which the infection rate (%) was investigated.

The results are shown in Table 7.

TABLE 7

| Agent tested | Amount of agent applied (ppm) | Infection rate (%) |
| --- | --- | --- |
| Compound (Ia) | 10 | 20 |
| Compound (Ib) | 10 | 20 |
| Compound (Ic) | 10 | 25 |
| Compound (Id) | 10 | 20 |
| Compound (Ie) | 2 | 20 |
| Folpet | 200 | 20 |
| Compound (Ia) + Folpet | 10 + 200 | 0 |
| Compound (Ib) + Folpet | 10 + 200 | 0 |
| Compound (Ic) + Folpet | 10 + 200 | 0 |
| Compound (Id) + Folpet | 10 + 200 | 0 |
| Compound (Ie) + Folpet | 2 + 200 | 0 |

Test Example 8

Each of plastic pots was filled with sandy loam and sown with apple (Fuji), followed by growing in a greenhouse for 20 days. A suspension of test agents prepared according to Formulation Example 22 was diluted to a predetermined concentration with water, and foliage application of the dilution was carried out so as to adhere the dilution sufficiently to the surfaces of leaves of the apple young seedling which had put out a fourth or fifth true leaf. Then, the young seedling was inoculated with a suspension of spores of apple scab fungus by spraying. After the inoculation, the young seedling was allowed to stand in the dark at 15° C. and a high humidity for 4 days and then grown under illumination for 15 days, after which the infection rate (%) was investigated.

The results are shown in Table 8.

TABLE 8

| Agent tested | Amount of agent applied (ppm) | Infection rate (%) |
| --- | --- | --- |
| Compound (Ia) | 0.8 | 20 |
| Compound (Ib) | 2 | 25 |
| Compound (Ic) | 5 | 25 |
| Compound (Id) | 5 | 25 |
| Compound (Ie) | 0.5 | 20 |
| Captan | 300 | 20 |
| Compound (Ia) + Captan | 0.8 + 300 | 0 |
| Compound (Ib) + Captan | 2 + 300 | 0 |
| Compound (Ic) + Captan | 5 + 300 | 0 |
| Compound (Id) + Captan | 5 + 300 | 0 |
| Compound (Ie) + Captan | 0.5 + 300 | 0 |

Test Example 9

Each of plastic pots was filled with sandy loam and sown with grape (Berry A), followed by growing in a greenhouse for 40 days. A wettable powder of test agents prepared according to Formulation Example 29 was diluted to a predetermined concentration with water, and foliage application of the dilution was carried out so as to adhere the dilution sufficiently to the surfaces of leaves of the grape young seedling which had put out three true leaves. Then, the young seedling was inoculated with a suspension of zoosporangia of grape downy mildew fungus by spraying. After the inoculation, the young seedling was allowed to stand overnight at 23° C. and a high humidity and then grown in a greenhouse for 7 days, after which the infection rate (%) was investigated.

The results are shown in Table 9.

TABLE 9

| Agent tested | Amount of agent applied (ppm) | Infection rate (%) |
| --- | --- | --- |
| Compound (Ia) | 20 | 25 |
| Compound (Ib) | 40 | 20 |
| Compound (Ic) | 100 | 20 |
| Compound (Id) | 40 | 20 |
| Compound (Ie) | 10 | 25 |
| Cymoxanil | 40 | 20 |
| Metalaxyl | 1 | 20 |
| Benalaxyl | 1 | 25 |
|  | 1 | 25 |
| Oxadixyl | 5 | 20 |
| Fosetyl aluminum | 100 | 25 |
| Compound (Ia) + Cymoxanil | 20 + 40 | 0 |
| Compound (Ib) + Cymoxanil | 40 + 40 | 0 |
| Compound (Ic) + Cymoxanil | 100 + 40 | 0 |
| Compound (Id) + Cymoxanil | 40 + 40 | 0 |
| Compound (Ie) + Cymoxanil | 10 + 40 | 0 |
| Compound (Ia) + Metalaxyl | 40 + 1 | 0 |
| Compound (Ie) + Metalaxyl | 10 + 1 | 0 |
| Compound (Ie) + Benalaxyl | 40 + 1 | 0 |
| Compound (Ie) + Ofurace | 10 + 1 | 0 |
| Compound (Ie) + Oxadixyl | 10 + 5 | 0 |
| Compound (Ia) + Fosetyl aluminum | 40 + 100 | 0 |
| Compound (Ie) + Fosetyl aluminum | 10 + 100 | 0 |

Test Example 10

Each of plastic pots was filled with sandy loam and sown with tomato (Ponterosa), followed by growing in a greenhouse for 20 days. A wettable powder of test agents prepared according to Formulation Example 35 was diluted to a predetermined concentration with water, and foliage application of the dilution was carried out so as to adhere the dilution sufficiently to the surfaces of leaves of the tomato young seedling which had put out two true leaves. Then, the young seedling was inoculated with a suspension of zoosporangia of tomato late blight fungus by spraying. After the inoculation, the young seedling was allowed to stand overnight at 23° C. and a high humidity and then grown in a greenhouse for 4 days, after which the infection rate (%) was investigated.

The results are shown in Table 10.

TABLE 10

| Agent tested | Amount of agent applied (ppm) | Infection rate (%) |
| --- | --- | --- |
| Compound (Ia) | 100 | 25 |
| Compound (Ib) | 40 | 20 |
| Compound (Ic) | 40 | 20 |
| Compound (Id) | 40 | 20 |
| Compound (Ie) | 5 | 25 |
| Metalaxyl | 5 | 20 |
| Compound (Ia) + Metalaxyl | 100 + 5 | 0 |
| Compound (Ib) + Metalaxyl | 40 + 5 | 0 |
| Compound (Ic) + Metalaxyl | 40 + 5 | 0 |
| Compound (Id) + Metalaxyl | 40 + 5 | 0 |
| Compound (Ie) + Metalaxyl | 5 + 5 | 0 |

Test Example 11

Each of plastic pots was filled with sandy loam and sown with cucumber (Sagamihanjiro), followed by growing in a greenhouse for 14 days. A wettable powder of test agents prepared according to Formulation Example 35 was diluted to a predetermined concentration with water, and foliage application of the dilution was carried out so as to adhere the dilution sufficiently to the surfaces of leaves of the grown cucumber young seedling. After air-drying, gray mold fungus was inoculated on the surfaces of leaves of the young seedling, and the young seedling was grown in the dark at 10° C. and a high humidity for 4 days, after which the infection rate (%) was investigated.

The results are shown in Table 11.

TABLE 11

| Agent tested | Amount of agent applied (ppm) | Infection rate (%) |
| --- | --- | --- |
| Compound (Ia) | 10 | 30 |
| Compound (Ib) | 200 | 20 |
| Compound (Ic) | 200 | 20 |
| Compound (Id) | 200 | 20 |
| Compound (Ie) | 20 | 25 |
| Fludioxonil | 0.5 | 20 |
| Pyrimetanil | 10 | 20 |
| Mepanipyrim | 5 | 20 |
| Fluazinam | 1 | 25 |
| Compound (Ia) + Fludioxonil | 10 + 0.5 | 0 |
| Compound (Id) + Fludioxonil | 200 + 0.5 | 0 |
| Compound (Ie) + Fludioxonil | 20 + 0.5 | 0 |
| Compound (Ia) + Pyrimetanil | 10 + 10 | 0 |
| Compound (Ib) + Pyrimetanil | 200 + 10 | 0 |
| Compound (Ie) + Pyrimetanil | 20 + 10 | 0 |
| Compound (Ia) + Mepanipyrim | 10 + 5 | 0 |
| Compound (Ic) + Mepanipyrim | 200 + 5 | 0 |
| Compound (Ie) + Mepanipyrim | 20 + 5 | 0 |
| Compound (Ia) + Fluazinam | 10 + 1 | 0 |
| Compound (Ie) + Fluazinam | 20 + 1 | 0 |

Test Example 12

Each of plastic pots was filled with sandy loam and sown with cucumber (Sagamihanjiro), followed by growing in a greenhouse for 14 days. A wettable powder of test agents prepared according to Formulation Example 41 was diluted to a predetermined concentration with water, and foliage application of the dilution was carried out so as to adhere the dilution sufficiently to the surfaces of leaves of the grown cucumber young seedling. After air-drying, each of gray mold fungi sensitive and tolerant, respectively, to benzimidazole type fungicidal compounds was inoculated on the surfaces of leaves of the young seedling, and the young seedling was grown in the dark at 10° C. and a high humidity for 4 days, after which the infection rate (%) was investigated.

The results are shown in Table 12.

TABLE 12

| Agent tested | Amount of agent applied (ppm) | Infection rate (%) | |
| --- | --- | --- | --- |
| | | Sensitive fungus | Resistant fungus |
| Compound (Ia) | 10 | 30 | 30 |
| Compound (Ib) | 200 | 20 | 20 |
| Compound (Ic) | 200 | 20 | 20 |
| Compound (Id) | 200 | 20 | 20 |
| Compound (Ie) | 20 | 25 | 25 |
| Benomyl | 10 | 20 | 100 |
| Carbendazim | 5 | 20 | 100 |
| Thiabendazole | 30 | 25 | 100 |

TABLE 12-continued

| Agent tested | Amount of agent applied (ppm) | Infection rate (%) Sensitive fungus | Infection rate (%) Resistant fungus |
|---|---|---|---|
| Thiophanate-methyl | 10 | 25 | 100 |
| Compound (Ia) + Benomyl | 10 + 10 | 0 | 0 |
| Compound (Ia) + Carbendazim | 10 + 5 | 0 | 0 |
| Compound (Ia) + Thiabendazole | 10 + 30 | 0 | 0 |
| Compound (Ia) + Thiophanate-methyl | 10 + 10 | 0 | 0 |
| Compound (Ib) + Benomyl | 200 + 10 | 0 | 0 |
| Compound (Ic) + Carbendazim | 200 + 5 | 0 | 0 |
| Compound (Id) + Thiophanate-methyl | 200 + 10 | 0 | 0 |
| Compound (Ie) + Benomyl | 20 + 10 | 0 | 0 |
| Compound (Ie) + Carbendazim | 20 + 5 | 0 | 0 |
| Compound (Ie) + Thiabendazole | 20 + 30 | 0 | 0 |
| Compound (Ie) + Thiophanate-methyl | 20 + 10 | 0 | 0 |

Test Example 13

Each of plastic pots was filled with sandy loam and sown with apple (Fuji), followed by growing in a greenhouse for 20 days. A suspension of test agents prepared according to Formulation Example 40 was diluted to a predetermined concentration with water, and foliage application of the dilution was carried out so as to adhere the dilution sufficiently to the surfaces of leaves of the apple young seedling which had put out a fourth or fifth true leaf. Then, the young seedling was inoculated with a suspension of spores of apple scab fungus by spraying. After the inoculation, the young seedling was allowed to stand in the dark at 15° C. and a high humidity for 4 days and then grown under illumination for 15 days, after which the infection rates investigated.

The results are shown in Table 13.

TABLE 13

| Agent tested | Amount of agent applied (ppm) | Infection rate (%) |
|---|---|---|
| Compound (Ia) | 1 | 20 |
| Compound (Ib) | 1 | 25 |
| Compound (Ic) | 1 | 30 |
| Compound (Id) | 5 | 20 |
| Compound (Ie) | 0.5 | 20 |
| Benomyl | 20 | 25 |
| Carbendazim | 20 | 25 |
| Thiophanate-methyl | 10 | 20 |
| Compound (Ia) + Benomyl | 1 + 20 | 0 |
| Compound (Ia) + Carbendazim | 1 + 20 | 0 |
| Compound (Ib) + Thiophanate-methyl | 1 + 10 | 0 |
| Compound (Ic) + Thiophanate-methyl | 1 + 10 | 0 |
| Compound (Id) + Thiophanate-methyl | 5 + 10 | 0 |
| Compound (Ie) + Benomyl | 0.5 + 20 | 0 |
| Compound (Ie) + Carbendazim | 0.5 + 20 | 0 |
| Compound (Ie) + Thiophanate-methyl | 0.5 + 10 | 0 |

Test Example 14

Each of plastic pots was filled with sandy loam and planted with a grape (Berry A) plant, and a wettable powder of test agents prepared according to Formulation Example 47 was diluted to a predetermined concentration with water and sprayed on the plant so as to adhere to the surfaces of leaves of the plant, after the plant put out a fourth leaf. After air-drying, the surfaces of the leaves were inoculated with a suspension of spores ($2 \times 10^5$ spores/ml) of grape powdery mildew fungus (*Uncinula necator*) by spraying. After the inoculation, the plant was grown at 24° C. for 3 weeks and then the infection rate (%) was investigated.

The results are shown in Table 14.

TABLE 14

| Agent tested | Amount of agent applied (ppm) | Infection rate (%) |
|---|---|---|
| Compound (Ia) | 1 | 20 |
| Compound (Ib) | 1 | 20 |
| Compound (Ic) | 1 | 20 |
| Compound (Id) | 1 | 25 |
| Compound (Ie) | 1 | 25 |
| Sulfur | 500 | 20 |
| Compound (Ia) + Sulfur | 1 + 500 | 0 |
| Compound (Ib) + Sulfur | 1 + 500 | 0 |
| Compound (Ic) + Sulfur | 1 + 500 | 0 |
| Compound (Id) + Sulfur | 1 + 500 | 0 |
| Compound (Ie) + Sulfur | 1 + 500 | 0 |

Test Example 15

A tomato plant (cultivar: Ponterosa) was planted in each pot and was sprayed with a sufficient volume of a dilution with a predetermined concentration of a wettable powder obtained according to Formulation Example 53, after the plant put out a third leaf. After air-drying of the spray mix, the surfaces of the leaves were inoculated with a suspension of spores ($5 \times 10^4$ spores/ml) of tomato late blight fungus (*Phytophthora infestans*) by spraying. After the inoculation, the plant was grown at 24° C. for 1 week and then the infection rate (%) was investigated.

The results are shown in Table 15.

TABLE 15

| Agent tested | Amount of agent applied (ppm) | Infection rate (%) |
|---|---|---|
| Compound (Ia) | 10 | 25 |
| Compound (Ib) | 50 | 25 |
| Compound (Ic) | 10 | 25 |
| Compound (Id) | 10 | 25 |
| Compound (Ie) | 10 | 25 |
| Copper oxychloride | 500 | 25 |
| Copper oxyquinolinolate | 50 | 25 |
| Compound (Ia) + Copper oxychloride | 10 + 500 | 0 |
| Compound (Ia) + Copper oxyquinolinolate | 10 + 500 | 0 |
| Compound (Ib) + Copper oxychloride | 50 + 500 | 0 |
| Compound (Ic) + Copper oxychloride | 10 + 500 | 0 |
| Compound (Id) + Copper oxychloride | 10 + 500 | 0 |
| Compound (Ie) + Copper oxychloride | 10 + 500 | 0 |
| Compound (Ie) + Copper oxyquinolinolate | 10 + 50 | 0 |

Test Example 16

Each of plastic pots was filled with sandy loam and planted with a grape (Berry A) plant, and a wettable powder of test agents prepared according to Formulation Example 53 was diluted to a predetermined concentration and sprayed on the plant so as to adhere to the surfaces of leaves of the plant, after the plant put out a fourth leaf. After air-drying, the surfaces of the leaves were inoculated with a suspension of spores (2×10⁵ spores/ml) of grape powdery mildew fungus (*Uncinula necator*) by spraying. After the inoculation, the plant was grown at 24° C. for 3 weeks and then the infection rate (%) was investigated.

The results are shown in Table 16.

TABLE 16

| Agent tested | Amount of agent applied (ppm) | Infection rate (%) |
|---|---|---|
| Compound (Ia) | 10 | 30 |
| Compound (Ib) | 50 | 25 |
| Compound (Ic) | 10 | 25 |
| Compound (Id) | 10 | 25 |
| Compound (Ie) | 10 | 25 |
| Copper oxychloride | 500 | 30 |
| Copper oxyquinolinate | 200 | 25 |
| Compound (Ia) + Copper oxychloride | 10 + 500 | 0 |
| Compound (Ia) + Copper oxyquinolinate | 10 + 200 | 0 |
| Compound (Ib) + Copper oxychloride | 50 + 500 | 0 |
| Compound (Ic) + Copper oxychloride | 10 + 500 | 0 |
| Compound (Id) + Copper oxychloride | 10 + 500 | 0 |
| Compound (Ie) + Copper oxychloride | 10 + 500 | 0 |
| Compound (Ie) + Copper oxyquinolinate | 10 + 200 | 0 |

Test Example 17

Each of plastic pots was filled with sandy loam and sown with cucumber (Sagamihanjiro), followed by growing in a greenhouse for 14 days. A wettable powder of test agents prepared according to Formulation Example 59 was diluted to a predetermined concentration with water, and foliage application of the dilution was carried out so as to adhere the dilution sufficiently to the surfaces of leaves of the grown cucumber young seedling. After air-drying, each of gray mold fungi sensitive and tolerant, respectively, to benzimidazole type fungicidal compounds was inoculated on the surfaces of leaves of the young seedling, and the young seedling was grown in the dark at 10° C. and a high humidity for 4 days, after which the infection rate (%) was investigated.

The results are shown in Table 17.

TABLE 17

| Agent tested | Amount of agent applied (ppm) | Infection rate (%) Sensitive fungus | Infection rate (%) Resistant fungus |
|---|---|---|---|
| Diethofencarb | 10 | 100 | 20 |
| Compound (Ia) | 10 | 30 | 30 |
| Compound (Ib) | 200 | 20 | 20 |
| Compound (Ic) | 200 | 20 | 20 |
| Compound (Id) | 200 | 20 | 20 |
| Compound (Ie) | 20 | 25 | 25 |
| Diethofencarb + Compound (Ia) | 10 + 10 | 0 | 0 |
| Diethofencarb + Compound (Ib) | 10 + 200 | 0 | 0 |
| Diethofencarb + Compound (Ic) | 10 + 200 | 0 | 0 |
| Diethofencarb + Compound (Id) | 10 + 200 | 0 | 0 |
| Diethofencarb + Compound (Ie) | 10 + 20 | 0 | 0 |

What is claimed is:

1. A fungicidal composition comprising, as active ingredients, synergistically effective amounts of (Ia) methyl α-methoxyimino-2[(2-methylphenoxy) methyl]-phenylacetate, and (b) at least one ethylenebis(dithiocarbamate) type fungicidal compound selected from zinc salt (Zineb), manganese salt (Maneb) or a salt with zinc and manganese (Mancozeb).

2. A fungicidal composition according to claim 1, wherein the amount of the ethylenebis(dithiocarbamate) is 0.01 to 100 parts by weight per part by weight of the compound (Ia).

3. A fungicidal composition according to claim 1, wherein the amount of the ethylenebis(dithiocarbamate) is 0.1 to 50 parts by weight per part by weight of the compound (Ia).

4. A fungicidal composition according to claim 1, wherein the amount of the ethylenebis(dithiocarbamate) is 1 to 20 parts of weight per part by weight of the compound (Ia).

5. A method for controlling plant diseases which comprises applying a fungicidal composition according to claim 1, to plants, soil or seeds.

* * * * *